United States Patent [19]

Ahmad

[11] Patent Number: 4,848,341
[45] Date of Patent: Jul. 18, 1989

[54] SUTURE CUTTER

[76] Inventor: Riyaz Ahmad, 9 Melrose Grove, Spinneyfield, Rotherham S60 3NA, England

[21] Appl. No.: 125,330

[22] Filed: Nov. 25, 1987

[30] Foreign Application Priority Data

Nov. 25, 1986 [GB] United Kingdom ................ 8628090

[51] Int. Cl.[4] ...................... A61F 17/32; A61B 17/06; B25F 3/00; B25B 7/22
[52] U.S. Cl. .................................. 128/340; 128/321; 128/354; 128/305; 30/125
[58] Field of Search ............... 128/305, 340, 346, 321; 30/125, 157, 124, 287, 288, 313, 130, 127, 128, 312; 7/129–132

[56] References Cited

U.S. PATENT DOCUMENTS

| 234,981 | 11/1880 | Harris et al. | 30/123 |
| 1,276,433 | 8/1918 | Stainbrook et al. | 30/125 |
| 1,364,829 | 4/1921 | Berg | 7/130 |
| 1,514,488 | 11/1924 | Wernmont | 7/130 |
| 3,600,806 | 8/1971 | Naccash | 30/294 |
| 3,651,811 | 3/1972 | Hildebrandt et al. | 128/305 |
| 3,879,846 | 4/1975 | Allen | 30/124 |
| 4,271,838 | 6/1981 | Lasner et al. | 128/318 |
| 4,316,324 | 2/1982 | Cochran | 30/287 |
| 4,478,221 | 10/1984 | Heiss | 128/340 |
| 4,669,470 | 6/1987 | Brandfield | 128/318 |

Primary Examiner—Edward M. Coven
Assistant Examiner—Gary Jackson
Attorney, Agent, or Firm—R. A. Giangiorgi

[57] ABSTRACT

A microsurgical suture cutting instrument comprising a blade means provided in a housing having a generally C-shaped configuration with the blade located with it and with cutting edge facing the open side of the housing.

6 Claims, 1 Drawing Sheet

SUTURE CUTTER

BACKGROUND OF THE INVENTION

This invention relates to a suture cutting instrument.

In order to apply a suture, a surgeon would ordinarily use one hand to hold a needle holder with thread and needle, and the other hand to hold forceps, and after applying the suture an assistant would cut the thread with a pair of scissors. This whole procedure is inconvenient and time-consuming, and there are many times when an assistant is not available, such as in busy casuality departments or as in the casualty departments of hospitals in many third world countries where there is a shortage of trained staff. A particular difficulty associated with microsurgery is the cutting of the thread after the suture has been applied. In ordinary surgery a surgeon would hold the thread with either a needle holder or tying forceps and an assistant would cut the thread leaving the surgeon ready to move immediately with the application of the next suture. With microsurgery an assistant must view the thread with the naked eye, or the microscope must be provided with an attachment whereby the assistant can view the thread along with the surgeon. Alternatively, the surgeon must put down one of the two instruments being used to apply the suture in order to pick up e.g. microscissors, and cut the thread himself. This is both inconvenient and time-consuming.

SUMMARY OF THE INVENTION

According to the present invention, a suture cutting instrument comprises a housing cutter means provided in the housing and accessible by the thread, said housing being located on one of the instruments ordinarily employed in the application of sutures.

Thus, the housing can be located at the non-operative end of tying forceps or at the end of one of the handles of a needle holder, and when all a surgeon needs to do is to reverse the instrument in his hand and apply the cutting means to the suture, and reverse the instrument again to recommence the application of the sutures.

Preferably, the housing has a generally C-shaped configuration with a blade located within it and with the cutting edge facing the open side of the housing. It is further preferred that two blades are provided located in the housing such as to provide a V-shaped cutting edge facing the open side of the housing.

The housing may be separately formed from an appropriate metal or plastics material, and suitably secured on an appropriate instrument, such as by providing dependent socket or clip means on the housing or dependent flange and locking screw means to enable it to be located on the end of an appropriate instrument, but equally, the housing may be formed integrally with the implement.

BRIEF DESCRIPTION OF THE DRAWINGS

Two embodiments of the invention will now be described with reference to the accompanying drawings, in which.

DESCRIPTION OF THE PREFERRED EMBODIMENT

Figure 1:
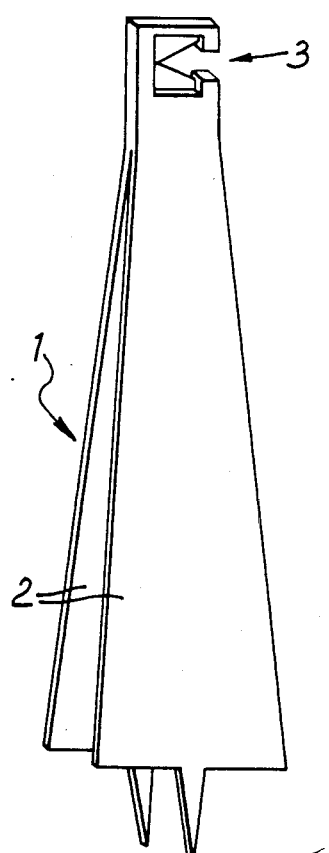
FIG. 1 is a perspective view of suture tying forceps provided with a suture cutter.
Figure 2:
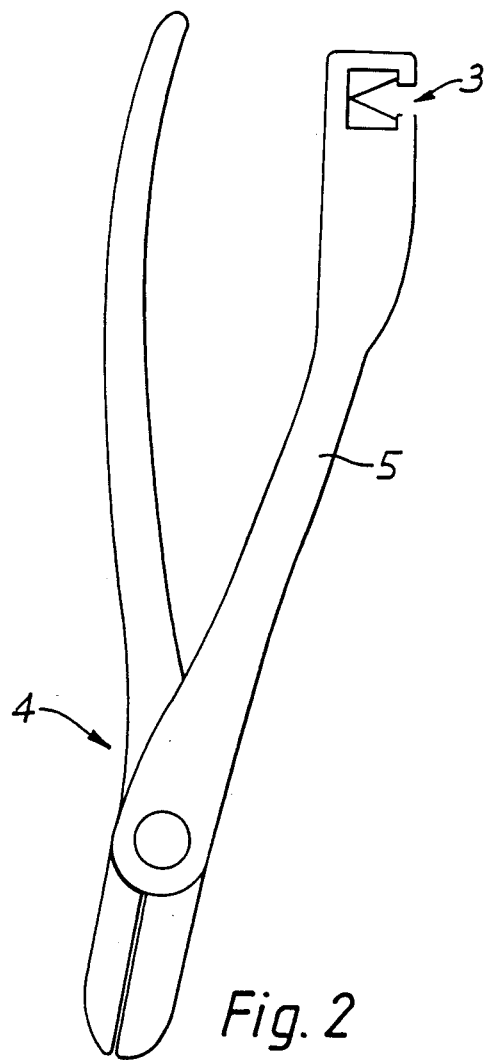
FIG. 2 is a perspective view of a suture needle holder provided with a suture cutter.
Figure 3:
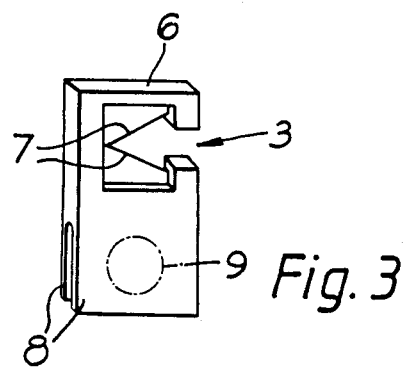
FIG. 3 is an enlarged view of a separately formed suture cutter.

In FIG. 1, suture tying forceps 1 of the type used in micro-surgery has two spring limbs 2 formed integrally or suitably secured together at their rearward ends. Located at the closed end is a suture cutter 3 and which, dependent on the material of the tying forceps, can be formed integrally with the limbs 2 or as is shown by FIG. 3, can be separately formed and suitably secured to the rearward end of the forceps. In FIG. 2 there is illustrated a needle holder 4, again of a type that would be used in micro-surgery, where a suture cutter 3 is provided at the end of one of its handles 5. Here again, the suture cutter can be formed integrally with the handle or separately formed and suitably secured in place.

As is shown by FIG. 3, the suture cutter comprises a generally C-shaped housing 6 in which blade means 7 are provided to present a generally V-shaped cutting edge, facing the access opening to the side of the housing. The blade may be a single blade with a V-shaped cutting edge, or may be two blade members each with a cutting edge and secured in the housing such that the blades combine to provide a V-shaped cutting edge.

It will be understood that it is the housing 6 that can be formed integrally on the forceps or the needle holder shown respectively in FIGS. 1 and 2. When the suture cutter is separately formed, it is provided with two dependent flanges 8 to overlie the ends of the forceps 1 or the end of the handle 5 of the needle holder 4, to serve as a clip or allow the holder to be secured in place by an appropriate adhesive, or other suitable means such as a locking screw as is indicated at 9.

Thus, in use in micro-surgery in particular, a surgeon will have a needle holder in one hand and tying forceps in the other when sutures are being applied, and viewed through a microscope. Once a suture has been tied, then on the one hand, the training lengths of thread can be gripped by the needle holder, and the tying forceps reversed by the surgeon in his hand, and the suture cutter applied to the thread lengths. On the other hand, the trailing lengths of thread can be gripped by the tying forceps, and the needle holder reversed in the surgeon's hand and the suture cutter applied to the thread.

In either instance, it will be appreciated that the task of severing sutures, particularly during microsurgery, is considerably simplified, and is under the full control of the surgeon himself, viewed through a microscope, and without the surgeon having to put one instrument down to pick up e.g. microscissors, and whereby to effect cutting of the thread.

I claim:

1. A microsurgical suture cutting instrument comprising a support element; a cutter housing separately formed and secured to said support element and accessible for cutting of microsurgical suture thread; said housing having a generally C-shaped configuration with an open side of said housing a cutting blade located within said housing and having a cutting edge facing said opening side of said housing for cutting said suture thread passed through said open housing side.

2. A suture cutting instrument as in claim 1 wherein two cutting blades are provided within the housing so located as to provide a V-shaped cutting edge facing the open side of the housing.

3. A microsurgical suture cutting instrument comprising suture tying forceps including first and second limbs spaced by an opening therebetween; a cutter housing separately formed and subsequently secured to said tying forceps, said housing having a generally C-shaped configuration with an open side of the housing separate from said forceps opening, and a cutting blade within said housing having a cutting edge facing said housing opening for cutting microsurgical thread.

4. A suture cutting instrument as in claim 3 wherein two cutting blades are provided within the housing so located as to provide a V-shaped cutting edge facing the open side of the housing.

5. A microsurgical suture cutting instrument comprising a needle holder having two handles; a cutter housing separately formed and subsequently secured to one of said handles and accessible for cutting of microsurgical suture thread; said housing having a generally C-shaped configuration with an open side of said housing, and a cutting blade located within said housing and having a cutting edge facing said open side of said housing for cutting said suture thread passed through said open housing side.

6. A suture cutting instrument as in claim 5, wherein two cutting blades are provided within the housing so located as to provide a V-shaped cutting edge facing the open side of the housing.

* * * * *